(12) United States Patent
Hoernig et al.

(10) Patent No.: US 10,792,001 B2
(45) Date of Patent: Oct. 6, 2020

(54) ARRANGEMENT WITH A GANTRY OF A MEDICAL IMAGING DEVICE AND AN OMNIDIRECTIONAL SUSPENSION, AS WELL AS A METHOD OF EXECUTING A TRAVEL MOVEMENT OF SUCH AN ARRANGEMENT

(71) Applicant: Siemens Healthcare GmbH, Erlangen (DE)

(72) Inventors: Mathias Hoernig, Erlangen (DE); Hans-Juergen Mueller, Pretzfeld (DE); Georg Wittmann, Herzogenaurach (DE); Franz Dirauf, Ebensfeld (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 459 days.

(21) Appl. No.: 15/497,571

(22) Filed: Apr. 26, 2017

(65) Prior Publication Data

US 2017/0325763 A1 Nov. 16, 2017

(30) Foreign Application Priority Data

May 11, 2016 (DE) .................. 10 2016 208 123

(51) Int. Cl.
  *A61B 6/00* (2006.01)
  *A61B 6/03* (2006.01)
  (Continued)

(52) U.S. Cl.
  CPC ............ *A61B 6/4405* (2013.01); *A61B 5/055* (2013.01); *A61B 6/032* (2013.01); *A61B 6/037* (2013.01);
  (Continued)

(58) Field of Classification Search
  CPC ... A61B 6/4405; A61B 6/4488; A61B 6/4417; A61B 5/055; A61B 6/037; A61B 6/032;
  (Continued)

(56) References Cited

U.S. PATENT DOCUMENTS

| 3,876,255 A | 4/1975 | Ilon |
| 7,188,998 B2* | 3/2007 | Gregerson ............... A61B 6/02 378/197 |

(Continued)

FOREIGN PATENT DOCUMENTS

| CN | 102595015 A | 7/2012 |
| DE | 60315642 T2 | 6/2008 |
| JP | 2002067962 A | 3/2002 |

OTHER PUBLICATIONS

Generation Robots ("Holononnic wheel for robot Lego Mindstorms NXT/EV3", May 16, 2014, retrieved from https://web.archive.org/web/20140516145741/https://www.generationrobots.com/en/401247-holonomic-wheel-for-lego-mindstorms-nxt-robot.html) (Year: 2014).*

(Continued)

*Primary Examiner* — Bill Thomson
*Assistant Examiner* — Aminah Asghar
(74) *Attorney, Agent, or Firm* — Harness, Dickey & Pierce, P.L.C.

(57) ABSTRACT

An arrangement includes a gantry of a medical imaging device and an omnidirectional suspension for moving the arrangement relative to a support.

31 Claims, 5 Drawing Sheets

(51) Int. Cl.
*A61B 50/13* (2016.01)
*A61B 5/055* (2006.01)

(52) U.S. Cl.
CPC .......... *A61B 6/4417* (2013.01); *A61B 6/4488* (2013.01); *A61B 50/13* (2016.02)

(58) Field of Classification Search
CPC ........... A61B 50/13; A61B 6/44; A61B 6/482; A61B 6/54
See application file for complete search history.

(56) References Cited

U.S. PATENT DOCUMENTS

| | | | |
|---|---|---|---|
| 2003/0235266 A1* | 12/2003 | Gregerson | A61B 6/035 378/4 |
| 2004/0076262 A1* | 4/2004 | Shao | A61B 6/037 378/196 |
| 2004/0170254 A1* | 9/2004 | Gregerson | A61B 6/032 378/197 |
| 2010/0208274 A1 | 8/2010 | Kindlein et al. | |
| 2010/0296632 A1* | 11/2010 | Bouvier | A61B 6/4405 378/198 |
| 2011/0154569 A1* | 6/2011 | Wiggers | A61B 6/0407 5/81.1 R |
| 2011/0200175 A1 | 8/2011 | Gregerson et al. | |
| 2012/0155616 A1 | 6/2012 | Cuppen | |
| 2015/0216746 A1 | 8/2015 | Dirauf | |
| 2017/0020410 A1* | 1/2017 | Pavoni | A61N 1/403 |
| 2017/0188988 A1* | 7/2017 | Aasen | A61B 6/032 |
| 2018/0035957 A1* | 2/2018 | Liu | F28F 3/12 |

OTHER PUBLICATIONS

German Office Action dated Feb. 15, 2017.
https://web.archive.org/web/20160504092221/http://www.imris.com/intraoperative-solutions/visius-ict. Published May 4, 2016.
Office Action for Chinese Patent Application No. 201710330895.9 dated Jan. 19, 2020 and English translation thereof.

* cited by examiner

ARRANGEMENT WITH A GANTRY OF A MEDICAL IMAGING DEVICE AND AN OMNIDIRECTIONAL SUSPENSION, AS WELL AS A METHOD OF EXECUTING A TRAVEL MOVEMENT OF SUCH AN ARRANGEMENT

PRIORITY STATEMENT

The present application hereby claims priority under 35 U.S.C. § 119 to German patent application number DE 102016208123.3 filed May 11, 2016, the entire contents of which are hereby incorporated herein by reference.

FIELD

Embodiments of the invention generally relates to an arrangement with a gantry of a medical imaging device, a system with such an arrangement, a method of executing a travel movement of such an arrangement and a method of executing a scanning movement, relative to a patient, of an imaging data acquisition unit that is arranged on a gantry of a medical imaging device.

BACKGROUND

Medical imaging devices, in particular computed tomography devices (CT devices) and magnetic resonance tomography devices (MRT devices), are generally fixed-mounted. However, mobile systems, in particular mobile X-ray devices, are increasingly being used in medical imaging and therapy. In particular, large medical devices in clinical facilities are increasingly being arranged in such a way that they are multifunctional and can be used across operating rooms (OP rooms).

As a result, these systems have the advantage of being movable between and usable in multiple OP rooms. It is thus possible, for example, for a patient to be examined using several different modalities without further movement of the patient positioning device and without transferring the patient. In addition these mobile systems, such as for example (intraoperative) MRT devices and CT devices, which are often suspended from the ceiling and mounted on rails, enable a few systems to cover several OP rooms and significant cost savings to be made as a result.

For special areas of application CT devices are also installed on fixed-mounted travel rails. To persons skilled in the art, this configuration is known by the term "sliding gantry". In this way a CT device can be moved linearly, in order to travel from an inoperative position into the working position, e.g. in a treatment room, or to be used alternatively in two different rooms. Installation of these travel rails, cable runs, etc. is often costly and time consuming. Travel movements are generally restricted to the fixed-mounted rails. The fixed-mounted travel rails and the double undercarriage of a sliding gantry can cause hygiene problems. One problem with rail-mounted systems resides in the lack of freedom with regard to their positioning. Rail-mounted systems typically only enable translation movements along the rail and rotational movements about the axis of the rail. Positionability is consequently severely limited. Costs for rail solutions are typically very high. In the event of spatial changes, a rail solution can often only be adapted at relatively high cost and is therefore not very flexible.

In addition to rail-mounted systems mobile CT devices are also available that can be moved on adjustable casters and manually steered to their place of use (e.g. an OP room). However, compared to fixed CT devices or CT devices with a sliding gantry, in many cases these mobile CT devices have limitations with regard to image quality, scanning volume or performance (including tube output). Possibilities for application are typically limited to certain scenarios, for example permanent allocation to an examination bed. Furthermore, with such systems hygiene problems can arise in the OP room as a result of the air-based cooling system.

SUMMARY

At least one embodiment of the invention enables improved positionability of a gantry of a medical imaging device.

Further advantageous aspects of the invention are covered in the claims.

One embodiment variant of the invention relates to an arrangement comprising a gantry of a medical imaging device and an omnidirectional suspension, with the omnidirectional suspension being embodied to move the arrangement relative to a support.

One embodiment variant of the invention relates to a method of executing a travel movement of an arrangement that has a gantry of a medical imaging device and an omnidirectional suspension for moving the arrangement relative to a support, the method comprising:
  Provision of at least one target position,
  Determination of suspension control commands on the basis of the at least one target position,
  Execution of the travel movement of the arrangement via the omnidirectional suspension on the basis of the suspension control commands.

One embodiment variant of the invention relates to a method of executing a scanning movement of an imaging data acquisition unit that is arranged on the gantry of a medical imaging device, relative to a patient who is positioned on a positioning device, the method comprising:
  Execution of a first part of the scanning movement by the gantry being displaced relative to the omnidirectional suspension via a positioning unit that is arranged on an omnidirectional suspension,
  Execution of a travel movement of the omnidirectional suspension relative to the patient positioning device along the direction of the scanning movement, and
  Execution of a second part of the scanning movement by the gantry being displaced relative to the omnidirectional suspension via the positioning unit.

One embodiment variant of the invention relates to a method of executing a scanning movement of an imaging data acquisition unit that is arranged on a gantry of a medical imaging device relative to a patient who is positioned on a patient positioning device, the method comprising:
  Execution of a first part of the scanning movement by the gantry being displaced relative to the omnidirectional suspension via a positioning unit that is arranged on an omnidirectional suspension,
  Execution M1 of a travel movement of the omnidirectional suspension relative to the patient positioning device along the direction of the scanning movement, and
  Execution of a second part of the scanning movement by the gantry being displaced relative to the omnidirectional suspension via the positioning unit.

One embodiment variant of the invention relates to a system having
  an arrangement according to an embodiment variant of the invention, a movement control unit that is embodied to control the omnidirectional suspension and/or the positioning unit.

A further embodiment variant of the invention relates to a system that is also embodied to execute a method in accordance with an embodiment variant of the invention.

A further embodiment variant of the invention relates to a system and furthermore has the patient positioning device and/or the medical imaging device.

According to one embodiment variant of the invention, the medical imaging device is selected from the group of imaging modalities that includes of an X-ray device, a C-arm X-ray device, a computed tomography device (CT device), a molecular imaging device (MI device) a single photon emission computed tomography device (SPECT device), a positron emission tomography device (PET device), a magnetic resonance tomography device (MRT device) and combinations thereof (in particular PET-CT device, PET-MR device). The medical imaging device can also have a combination of an imaging modality that is for example selected from the group of imaging modalities, and an irradiation modality. The irradiation modality in this case can for example be an irradiation unit for therapeutic irradiation.

In the context of the invention, features that are described in relation to various embodiment variants of the invention and/or various claim categories (device, method, etc.) can be combined to form further embodiment variants of the invention. In other words, the physical claims, even with the features that are described or claimed in connection with a method, can be developed. In such cases functional features of an inventive method can be executed by appropriately embodied physical components. In addition to the embodiment variants of the invention expressly described in this application a plurality of other embodiment variants of the invention that it is possible for a person skilled in the art to attain without departing from the area of the invention, to the extent that the area of the invention is specified by the claims.

Use of the indefinite article "a" or "an" does not preclude the existence of one or even more of the feature in question. Use of the term "have" or "has" does not preclude the terms linked by the term "have" or "has" being identical. For example, the medical imaging device has the medical imaging device. Use of the term "unit" does not preclude the object to which the term "unit" refers having several components that are spatially separated from one another.

BRIEF DESCRIPTION OF THE DRAWINGS

The invention is described in more detail once again below with the aid of example embodiments and with reference to the attached figures. The representation of the figures is schematic and highly simplified as well as not necessarily to scale.

In the drawings.

DETAILED DESCRIPTION OF THE EXAMPLE EMBODIMENTS

Figure 1:
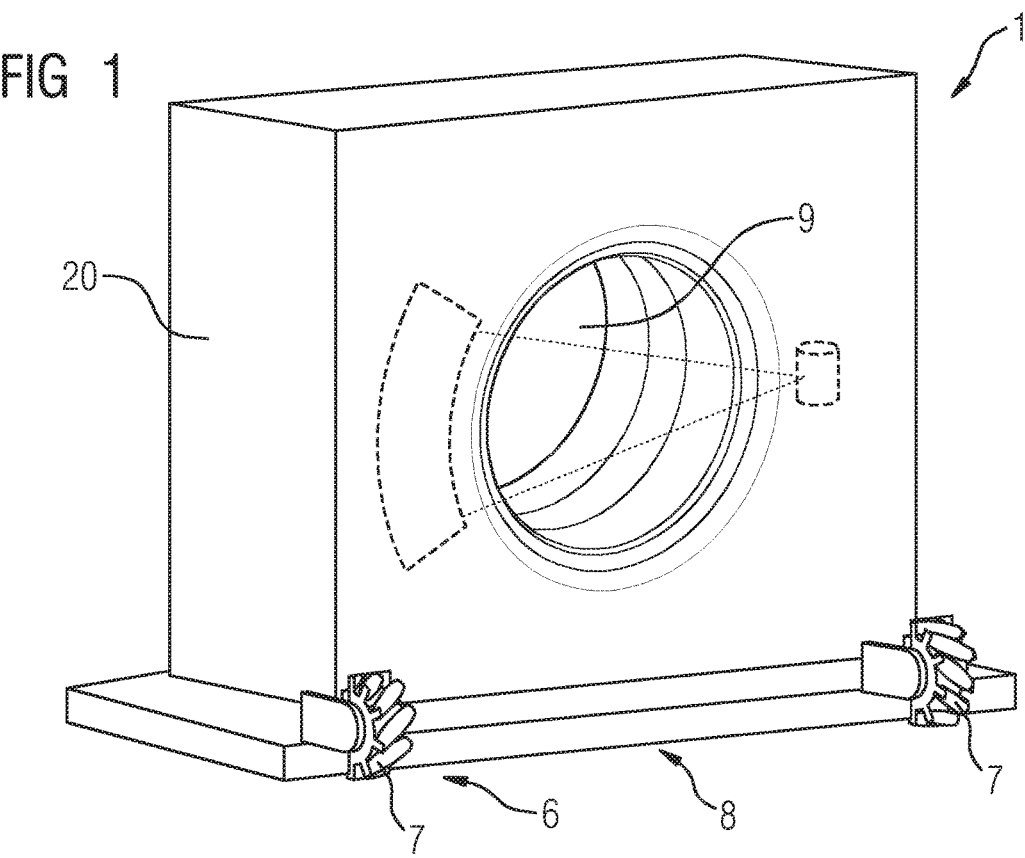
FIG. 1 shows a schematic representation of an arrangement according to a first embodiment variant of the invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

One embodiment variant of the invention relates to an arrangement having a gantry of a medical imaging device and an omnidirectional suspension, with the omnidirectional suspension being embodied to move the arrangement relative to a support. According to one embodiment variant of the invention the omnidirectional suspension is embodied to provide adjustable mounting of the gantry relative to the support. In particular, an arrangement is hereby disclosed that has a gantry of a medical imaging device and an omnidirectional suspension, with the gantry being adjustably mounted relative to a support via the omnidirectional suspension.

The gantry can for example be arranged directly and/or indirectly on the omnidirectional suspension. For example, the gantry can then be arranged indirectly on the omnidirectional suspension if the gantry is arranged directly on an intermediately mounted unit, with the intermediately mounted unit being arranged directly on the omnidirectional suspension. The intermediately mounted unit can in particular be the positioning unit and/or the stabilizing unit.

In an omnidirectional suspension the drive of the omnidirectional suspension and/or the wheels of the omnidirectional suspension are typically embodied to enable omnidirectional travel movement. In an omnidirectional travel movement the omnidirectional suspension can, starting from any position at which it has arrived, typically continue in any direction that lies on a sufficiently flat plane that is defined by the support and is not blocked.

The support can for example be a floor of a medical examination room, in particular of an OP room, and/or a floor of a hospital. The support can for example have, at least in some sections, a floor mat, a floor plate, a floor covering or similar, or combinations thereof.

The arrangement according to an embodiment of the invention can be understood as being a mobile gantry of a medical imaging device. Such an arrangement can have features that are comparable to those of a fixed gantry and at the same time are not subject to the limitations of a sliding gantry. U.S. Pat. No. 9,554,953 issued Jan. 31, 2017 is directed to a mobile medical device and method of controlling movement, the entire contents of which are hereby incorporated herein by reference.

For the solution according to at least one embodiment of the invention, no mechanical guiding elements, in particular no rails, are required. In comparison with the solution constrained by rails the solution according to the invention can be implemented with greater ease of installation and at less cost, requires less room and has improved positionability. Moreover, the solution according to the invention is flexibly adaptable, and at relatively low cost, to building alterations, for example in an operating room and/or in a clinic, and/or to changes in the intervention scenario, for example on the operating table.

An embodiment of the invention enables improved precision in comparison with a conventional mobile gantry, especially during a travel movement and during the positioning of the arrangement relative to a patient positioning device, improved image quality and improved performance of the medical imaging device. An embodiment of the invention also enables optimal integration into clinical procedures and improved support of applications of the medical imaging device. Many different application fields are possible for embodiment variants of the invention, in diagnostics, in treatment and in therapy. In particular, embodiment variants of the invention can be employed in radiology, in OP rooms, in treatment rooms, in emergency rooms, in sickbays, on the ward, in an oncology radiation booth or in similar places or across several such places.

One embodiment variant of the invention provides that the omnidirectional suspension has at least one omnidirectional wheel and/or at least one omnidirectional omnidrive module. One embodiment variant of the invention provides that the omnidirectional suspension is based on at least one omnidirectional wheel and/or on at least one omnidirectional omnidrive module. One embodiment variant of the invention provides that the at least one omnidirectional wheel is an omniwheel or a Mecanum wheel.

One embodiment variant of the invention provides that the omnidirectional suspension has a set of omniwheels and/or a set of Mecanum wheels. The at least one omnidirectional wheel can in particular be a set of omnidirectional wheels. The at least one omnidirectional omnidrive module can in particular be a set of omnidirectional omnidrive modules.

An omnidrive module can be understood as being, in particular, an integrated assembly that has a wheel, a first drive unit for driving a rotational movement of the wheel about a first rotating axis and a second drive unit for driving a rotational movement of the wheel about a second rotating axis. The first rotating axis is perpendicular to the plane of the wheel and leads through the center of the wheel. The second rotating axis is perpendicular to the first rotating axis.

The omnidrive module is typically arranged relative to a support upon which the wheel rolls in such a way that the first rotating axis is essentially parallel to the support, for example horizontal, and that the second rotating axis is essentially perpendicular to the support, for example vertical. It is thus possible both for the wheel to roll on the support and for a steering maneuver of the wheel to be driven. In the context of this application a wheel of the omnidirectional suspension is also understood as being, in particular, an omnidrive module of the omnidirectional suspension.

An omniwheel typically has a running surface formed of casters of which each of the rotating axes is arranged essentially perpendicular to the rotating axis of the omniwheel. This allows low friction movement of the wheel along the rotating axis of the omniwheel.

A Mecanum wheel typically has a running surface that is formed of casters, of which each of the rotating axes is arranged at an oblique angle, essentially of 45 degrees, to the rotating axis of the Mecanum wheel. Examples of Mecanum wheels are described in particular in U.S. Pat. No. 3,876,255, the entire contents of which are hereby incorporated herein by reference.

Alternatively or in addition, the omnidirectional suspension can have at least one conventional wheel and/or be based on at least one conventional wheel. The wheels of the omnidirectional suspension can for example each be steered and/or controlled individually and/or in groups.

One embodiment variant of the invention provides that one or more wheels of the omnidirectional suspension is in each case detachable from the omnidirectional suspension and/or is replaceable while the gantry is mounted relative to the support via the omnidirectional suspension, in particular without the omnidirectional suspension's having to be raised relative to the support.

One embodiment variant of the invention provides an arrangement and furthermore includes a positioning unit arranged on the omnidirectional suspension unit that is embodied to adjust a position of the gantry relative to the omnidirectional suspension and/or to adjust an orientation of the gantry relative to the omnidirectional suspension.

One embodiment variant of the invention provides that the positioning unit has a linear drive for the forward movement of the gantry relative to the omnidirectional suspension. In particular, the gantry can be connected to the omnidirectional suspension by way of the linear drive. According to one embodiment variant of the invention the gantry can be displaced by way of the linear drive in order to execute a scanning movement, for example along a system axis of the medical imaging device.

One embodiment variant of the invention provides that the positioning unit has a lifting device for the lifting movement of the gantry relative to the omnidirectional suspension. According to one embodiment variant of the invention the height of the gantry relative to the omnidirectional suspension can be adjusted via the lifting device. The lifting device can for example be a mechanical lifting device and/or be arranged on the load receiving unit.

One embodiment variant of the invention provides that the omnidirectional suspension has a load receiving unit that is embodied for the positive receiving of the gantry and/or of the positioning unit. By way of the load receiving unit a gantry of a medical imaging device of which the features and performance are comparable with and/or identical to those of a fixed gantry can be arranged in a simple manner on the omnidirectional suspension.

According to one embodiment variant of the invention, the wheels of the omnidirectional suspension are arranged on the load receiving unit. One embodiment variant of the invention provides that the load receiving unit is in the form of a plate and/or in the form of a frame and/or that the wheels of the omnidirectional suspension in each case are arranged underneath and/or at the side of the load receiving unit. One embodiment variant of the invention provides that the load receiving unit is embodied so as to be modular for several different medical imaging modalities, in each case for the positive receiving of the gantry of the medical imaging modality. One embodiment variant of the invention provides that the omnidirectional suspension is formed of wheels, with each of the wheels of the omnidirectional suspension being connected to a support frame of the gantry, in each case independently of the other wheels of the omnidirectional suspension.

One embodiment variant of the invention provides that the omnidirectional suspension has a loading unit that is embodied to load the gantry and/or the positioning unit. According to one embodiment variant of the invention the loading unit is embodied for the autonomous and/or the semiautonomous loading of the gantry and/or of the positioning unit, for example on the basis of information on the scenario.

For example, the loading unit can be embodied to unload the gantry and/or the positioning unit from the omnidirectional suspension, in particular in order to place it on the support and/or on a supporting device. For example, the loading unit can be embodied to load the gantry and/or the positioning unit onto the omnidirectional suspension, in particular to lift it from the support and/or from a supporting device. The loading unit can for example have a roller track, a conveyor belt, a rail-mounted wagon, grab buckets, hooks or similar, or combinations thereof.

One embodiment variant of the invention provides an arrangement and furthermore includes a stabilizing unit for stabilizing a height of the gantry and/or an inclination of the gantry in order to correct any unevenness of the support. In particular, the stabilizing unit can be embodied so as automatically to stabilize height and/or inclination of the gantry in order to correct any unevenness of the support.

One embodiment variant of the invention provides that the stabilizing unit
  has an unevenness recording module for recording unevenness measurement data that relates to unevenness of the support, and
  an unevenness correcting module for correcting unevenness on the basis of the unevenness measurement data.

The stabilizing unit can for example have fast acting actuators for correcting the unevenness. The stabilizing unit can for example stabilize the height of the gantry and/or the inclination of the gantry on the basis of localization measurement data and/or inclinometer measurements of the gantry.

One embodiment variant of the invention provides that the omnidirectional suspension has an environment information recording module for recording environment information that relates to the environment of the omnidirectional suspension. According to one embodiment variant of the invention the omnidirectional suspension is embodied for autonomous or semiautonomous movement on the basis of the environment information. The environment information recording module can for example have a contactless measurement system, sensors, in particular optical sensors, a camera or similar, or combinations thereof. The environment information recording module can for example be embodied for the localization and/or identification of the gantry and/or of obstacles. The contactless measurement system can for example be embodied for the continuous precise measurement of the position and/or of the orientation of the gantry and/or of the omnidirectional suspension, in particular relative to a patient positioning device. As a result, autonomous or semiautonomous travel movements of the omnidirectional suspension to provided target positions are possible. In this way it is possible, in particular, for obstacles to be traveled around and collisions avoided.

One embodiment variant of the invention provides that the omnidirectional suspension is embodied for autonomous travel and/or for semiautonomous travel. As a result, the arrangement can be positioned via autonomous and/or semiautonomous travel movements, in particular relative to a patient positioning device.

One embodiment variant of the invention provides an arrangement and furthermore includes an energy storage unit for supplying power to the omnidirectional suspension and/or to the gantry. As a result, cordless power supply, in particular of the omnidirectional suspension and/or of the gantry, is possible. The energy storage unit can for example have battery cells, capacitors, chemical compounds designed to store energy, mechanical systems designed to store energy, for example a flywheel or similar, or combinations thereof. The energy storage unit can be charged, for example wired by way of a plug and socket device, in particular via a docking station, or via a cordless, in particular inductive, charging device. Optionally, for continuous long term operation, power can be supplied and/or data can be transferred during connection to the mains via a detachable cable connection that can, in particular, comprise optical fibers for data transfer, it being possible for the energy storage unit to be charged at the same time.

One embodiment variant of the invention provides an arrangement and furthermore includes a data transfer unit for the transfer of data from the omnidirectional suspension and/or to the omnidirectional suspension and/or for the transfer of data from the gantry and/or to the gantry. The data transfer can for example take place wirelessly, in particular via radio waves or modulated light, for example infrared light. In particular, it is possible for imaging data and/or reconstructed image data to be transferred wirelessly in this way, from the gantry to a fixed unit relative to the support, or on a network.

One embodiment variant of the invention provides an arrangement and furthermore includes a heat storage unit and a cooling unit that is embodied for the cooling of a component of the gantry by heat transfer from the component to the heat storage unit. As a result, mobile ambient air-independent cooling of the gantry, in particular of the radiation source and/or of the radiation detector, is possible. The heat storage unit can for example be arranged in the gantry in such a way as to be replaceable and/or regeneratable. The heat storage unit can for example have a latent heat storage system, in particular salt and/or paraffin, a thermochemical storage system or similar, or combinations thereof.

One embodiment variant of the invention provides an arrangement and furthermore includes an air flow guidance unit for guiding an air flow for cooling a component of the gantry, with the air flow guidance unit having at least one exit for the air flow in the area of the support. By way of the air flow, heat transfer from the component of the gantry to the air in the vicinity of the gantry can take place. Preferably, the air flow exits laminarly through the at least one exit in the vicinity of the support and/or at a low flow speed. This can be assisted by suitable air flow elements that generate laminar flow in front of the at least one exit. In this way, hygiene problems caused by air turbulence, in particular in the OP room, can be avoided or reduced.

One embodiment variant of the invention provides a combined cooling system for cooling a component of the gantry, with the combined cooling system having the heat storage unit and the air flow guidance unit. Heat can be buffered, in particular in the event of brief power peaks of the component, via the heat storage unit. The heat can be released into the environment, in particular via a laminar air flow, via the air flow guidance unit.

One embodiment provides an arrangement and furthermore includes a cooling fluid attachment unit that is embodied to receive and/or to release a cooling fluid for cooling a component of the gantry. In particular for applications with strict requirements in relation to a sterile environment, the cooling of the component of the gantry can be effected by the circulation of a cooling fluid fed in from outside via the cooling fluid attachment unit. The cooling of the component of the gantry can for example be effected directly by the cooling fluid and/or indirectly using a heat exchanger. In particular, the gantry can have a heat exchanger for transferring heat from a closed cooling circuit within the gantry to the cooling fluid. For example, heat from a closed cooling circuit for cooling the component of the gantry can be transferred to the cooling fluid via the heat exchanger.

One embodiment variant of the invention relates to a method of executing a travel movement of an arrangement that has a gantry of a medical imaging device and an omnidirectional suspension for moving the arrangement relative to a support, the method comprising:

Provision of at least one target position,
Determination of suspension control commands on the basis of the at least one target position,
Execution of the travel movement of the arrangement via the omnidirectional suspension on the basis of the suspension control commands.

The arrangement can thus move, in particular fully automatically, into working positions and inoperative positions in different rooms of a building, autonomously and precisely orient itself for the execution of scanning movements and execute scanning movements. The arrangement is thus flexible within a room, for example an OP room, and can be moved beyond the room. The at least one target position can in particular be an organized list of waypoints forming a route. Provision of the at least one target position can for example be effected by programming or saving the at least one target position. The provision of the at least one target position can for example include selection of the at least one target position.

Such a selection can for example be effected by way of a user interface, for example with the aid of a mouse click and/or with the aid of a touch sensitive screen. For example, a list or a card with available target positions can be displayed via the user interface. Alternatively or in addition, such a selection can be effected automatically or semi-automatically, for example as a function of a clinical procedure. For example, recurrent positions of the arrangement can thus be saved and/or programmed and, if required, be selected by personnel via the user interface.

One embodiment variant of the invention relates to a method and furthermore comprises:
Recording of at least one item of environment information that relates to the environment of the omnidirectional suspension,
with the suspension control commands also being determined on the basis of the at least one item of environment information.

One embodiment variant of the invention provides that the determination of suspension control commands involves adaptive route planning. In particular, obstacles can be traveled around with the aid of adaptive planning.

One embodiment variant of the invention provides that the environment information is recorded autonomously by way of the omnidirectional suspension and/or the suspension control commands of the omnidirectional suspension are determined autonomously. The travel movement, for example to a docking station, an inoperative position or a working position, can be carried out fully automatically and/or autonomously.

One embodiment variant of the invention relates to a method of executing a scanning movement of an imaging data acquisition unit that is positioned on a gantry of a medical imaging device, relative to a patient who is positioned on a patient positioning device, with the gantry being adjustably mounted relative to a support via an omnidirectional suspension, it being possible for the scanning movement to be executed by the gantry being moved relative to the patient positioning device via the omnidirectional suspension.

One embodiment variant of the invention provides that imaging data on an area of the patient to be displayed is acquired during the scanning movement via the imaging data acquisition device. In particular, the scanning movement can be executed along a system axis of the medical imaging device and/or along a longitudinal direction of the patient positioning device. In particular, the scanning movement can be executed automatically and/or autonomously via the omnidirectional suspension. According to one embodiment variant of the invention, position data and/or environment information is transferred from the omnidirectional suspension to the medical imaging device continuously during the scanning movement. On the basis thereof, the scanning movement can for example be controlled, monitored and/or taken into account during the processing of the imaging data acquired during the scanning movement.

One embodiment variant of the invention relates to a method of executing a scanning movement of an imaging data acquisition unit that is arranged on the gantry of a medical imaging device, relative to a patient who is positioned on a positioning device, the method comprising:

Execution of a first part of the scanning movement by the gantry being displaced relative to the omnidirectional suspension via a positioning unit that is arranged on an omnidirectional suspension, Execution of a travel movement of the omnidirectional suspension relative to the patient positioning device along the direction of the scanning movement, and Execution of a second part of the scanning movement by the gantry being displaced relative to the omnidirectional suspension via the positioning unit.

One embodiment variant of the invention provides that the positioning unit has a linear drive for the forward movement of the gantry relative to the omnidirectional suspension and that the first part and the second part of the scanning movement are executed in each case by the gantry being displaced relative to the omnidirectional suspension via the linear drive. In this way it is possible, in particular if the length of the forward movement of the linear drive is not sufficient, for a scanning movement to be executed fully automatically in several successive parts, with the omnidirectional suspension being moved a certain distance in the scanning direction after each part of the scanning movement, and a further part of the scanning movement then being executed with the linear drive.

One embodiment variant of the invention relates to a system having an arrangement according to an embodiment variant of the invention, a movement control unit that is embodied to control the omnidirectional suspension and/or the positioning unit.

According to one embodiment variant of the invention, fully automatic control functions with which the travel movements can be executed, for example for positionings, and/or the scanning movements, can be executed, in particular autonomously or semiautonomously, via the movement control unit.

According to one embodiment variant of the invention, the movement control unit is embodied to control travel movements of the omnidirectional suspension, in particular in relation to three degrees of freedom. The three degrees of freedom can in this case include two translational degrees of freedom on a plane defined by the support, for example an essentially horizontal plane, and/or one rotational degree of freedom, for example about an essentially vertical axis.

According to one embodiment variant of the invention the movement control unit is embodied to control the respective wheel revolutions of the wheels of the omnidirectional suspension individually and simultaneously. According to one embodiment variant of the invention the movement control unit is embodied to control the respective steering angles of the wheels of the omnidirectional suspension individually and simultaneously. According to one embodiment variant of the invention several wheels of the omnidirectional suspension in relation to the drive and/or in relation to the controls can be combined into a wheel group.

A further embodiment variant of the invention relates to a system that is also embodied to execute a method in accordance with an embodiment variant of the invention.

A further embodiment variant of the invention relates to a system and furthermore has the patient positioning device and/or the medical imaging device.

According to one embodiment variant of the invention the system includes a cooling fluid supply unit that is embodied to be attached to the cooling fluid attachment unit of the arrangement and to feed in a cooling fluid for cooling a component of the gantry.

One embodiment variant of the invention provides that a position reference unit is arranged in the area of the patient positioning device as a position reference for an image reconstruction in such a way that imaging data which relate to the position reference unit can be acquired during the execution of a method according to an embodiment variant of the invention. According to one embodiment variant of the invention a position reference unit is arranged on the patient positioning device and/or in the vicinity of the patient positioning device as a position reference for an image reconstruction in such a way that imaging data which relate to the position reference unit can be acquired during the scanning movement.

With the aid of the position reference unit it is possible to assign a reference position to each of various imaging data subsets acquired at different positions of the gantry relative to the patient positioning device. On the basis of the respective reference positions it is possible for various imaging data subsets to be combined, for example, into an imaging dataset comprising several positions of the gantry relative to the patient positioning device. Alternatively or in addition, the scanning movement can be controlled and/or monitored, for example on the basis of the reference position. In particular it is possible for the position reference unit to be identifiable in an image that has been reconstructed on the basis of the imaging data. The position reference unit can for example be in the form of a linear marker extending in the scanning direction. A thin wire or rod that is arranged on the patient positioning device, in particular on the patient positioning plate, is suitable for this.

According to one embodiment variant of the invention, the medical imaging device is selected from the group of imaging modalities that includes of an X-ray device, a C-arm X-ray device, a computed tomography device (CT device), a molecular imaging device (MI device) a single photon emission computed tomography device (SPECT device), a positron emission tomography device (PET device), a magnetic resonance tomography device (MRT device) and combinations thereof (in particular PET-CT device, PET-MR device). The medical imaging device can also have a combination of an imaging modality that is for example selected from the group of imaging modalities, and an irradiation modality. The irradiation modality in this case can for example be an irradiation unit for therapeutic irradiation.

According to one embodiment variant of the invention the medical imaging device has an imaging data acquisition unit that is embodied to acquire the imaging data. In particular, the imaging data acquisition unit can have a radiation source and a radiation detector. One embodiment variant of the invention provides that the radiation source is embodied to emit and/or to stimulate radiation, in particular electromagnetic radiation, and/or that the radiation detector is embodied to detect radiation, in particular electromagnetic radiation. The radiation can for example reach from the radiation source to an area to be displayed and/or reach the radiation detector after interacting with the area to be displayed. During interaction with the area to be displayed the radiation is modified and thus becomes the carrier of information relating to the area to be displayed. During the interaction of the radiation with the detector this information is recorded in the form of the first imaging data.

With computed tomography devices and C-arm X-ray devices in particular, the first imaging data can be projection data, the imaging data acquisition unit a projection data acquisition unit, the radiation source an X-ray source and the radiation detector an X-ray detector. The X-ray detector can, in particular, be a quantum counting and/or an energy-resolved X-ray detector. Without limiting the general inventive concept, a computed tomography device is named in some of the embodiment variants of the invention that are described as an example of a medical imaging device. In a magnetic resonance tomography device in particular, the first imaging data can be a magnetic resonance dataset, the imaging data acquisition unit a magnetic resonance data acquisition unit, the radiation source a first high frequency antenna unit and the radiation detector the first high frequency antenna unit and/or a second high frequency antenna unit.

The gantry of a medical imaging device typically has a supporting structure upon which are arranged, in particular, components of the imaging data acquisition unit, in particular the radiation source and/or the radiation detector. The supporting structure of the gantry typically has such high rigidity and strength that the components of the imaging data acquisition device can be arranged, both relative to one another and relative to an area to be displayed, in a geometry that is sufficiently defined for imaging. In a computed tomography device the gantry typically has a supporting frame and a rotor positioned so as to be rotatable relative to the supporting frame, with the radiation source and the radiation detector being arranged on the rotor. Optionally, the gantry can have a tilting frame positioned so as to be tiltable relative to the supporting frame, with the rotor being arranged on the tilting frame.

In a C-arm X-ray device the gantry typically has a supporting frame and a C-arm positioned so as to be swivelable relative to the supporting frame, with the radiation source and the radiation detector being positioned on the C-arm.

In a magnetic resonance tomography device, the gantry typically has a supporting frame on which the main magnet and a first high frequency antenna unit are arranged, with the first high frequency antenna unit being embodied in a form known to persons skilled in the art by the term "body coil".

FIG. 1 shows a schematic representation of an arrangement 1 according to a first embodiment variant of the invention.

The first embodiment variant of the invention relates to an arrangement 1 that has a gantry 20 of a medical imaging device 2 and an omnidirectional suspension 6 for moving the arrangement 1 relative to a support 8.

Figure 2:
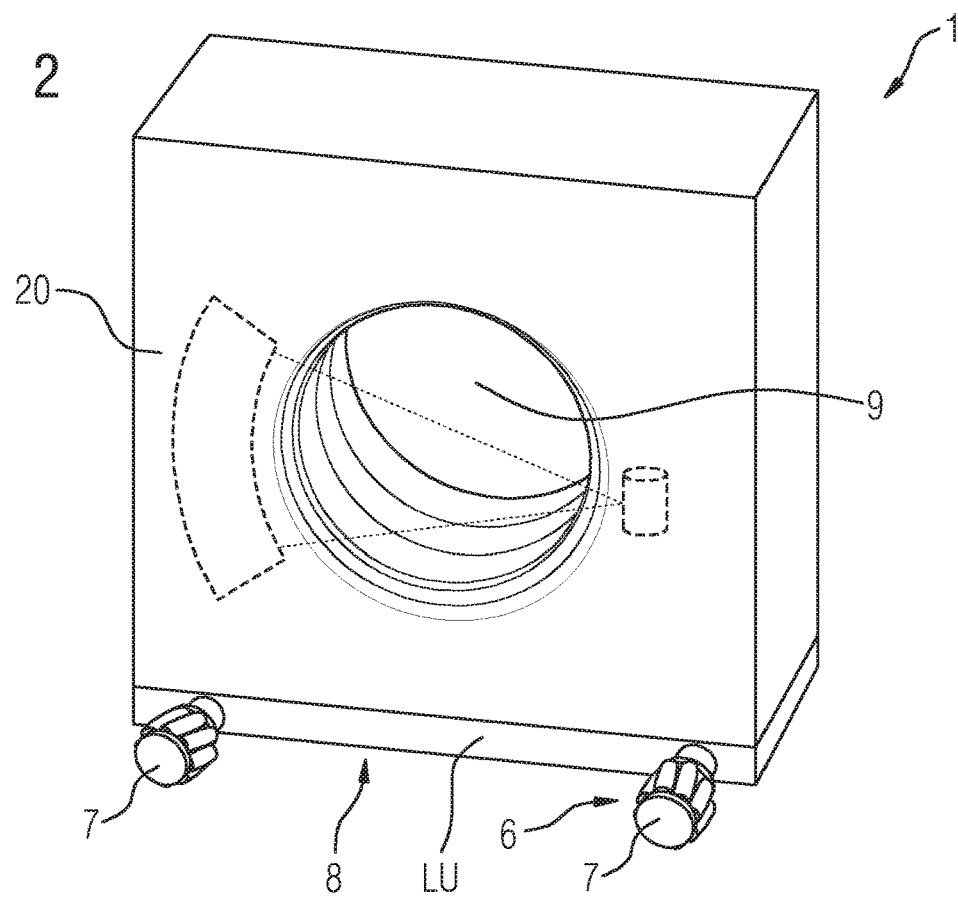
FIG. 2 shows a first view of a schematic representation of an arrangement according to a second embodiment variant of the invention.
Figure 3:
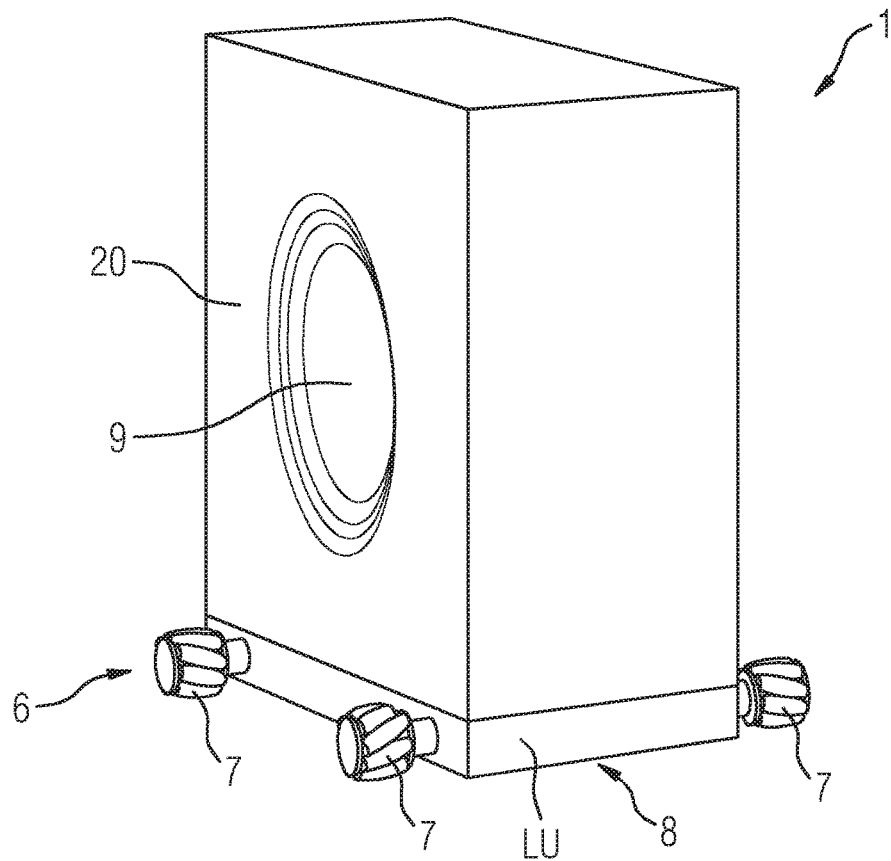
FIG. 3 shows a second view of a schematic representation of the arrangement according to the second embodiment variant of the invention.

FIG. 2 and FIG. 3 each show a view of a schematic representation of an arrangement 1 according to a second embodiment variant of the invention. According to the second embodiment variant of the invention, the omnidirectional suspension has a set of Mecanum wheels 7 with a total of four Mecanum wheels 7 and a load receiving unit LU that is embodied that is embodied for the positive receiving of the gantry 20 and of the positioning unit PU.

Figure 4:
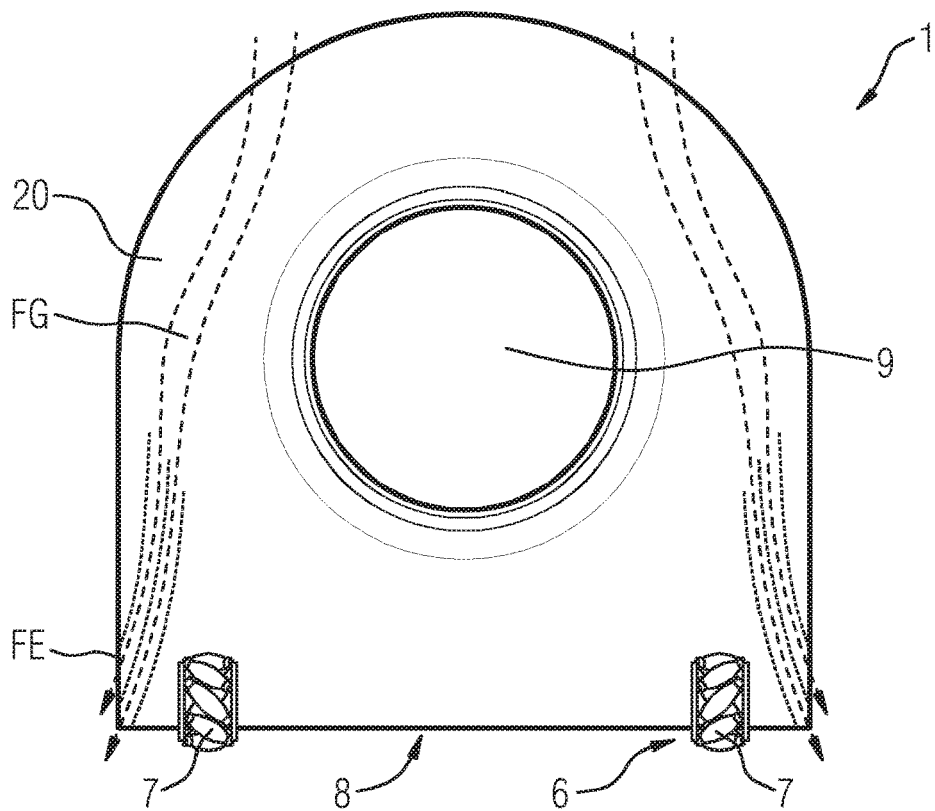
FIG. 4 shows a schematic representation of an arrangement according to a third embodiment variant of the invention.

FIG. 4 shows a schematic representation of an arrangement 1 according to a third embodiment variant of the invention.

The third embodiment variant of the invention relates to an arrangement 1 and furthermore includes an air flow guidance unit FG for guiding an air flow for cooling a component of the gantry 20, with the air flow guidance unit FG having at least one exit FE for the air flow in the area of the support 8.

Figure 5:
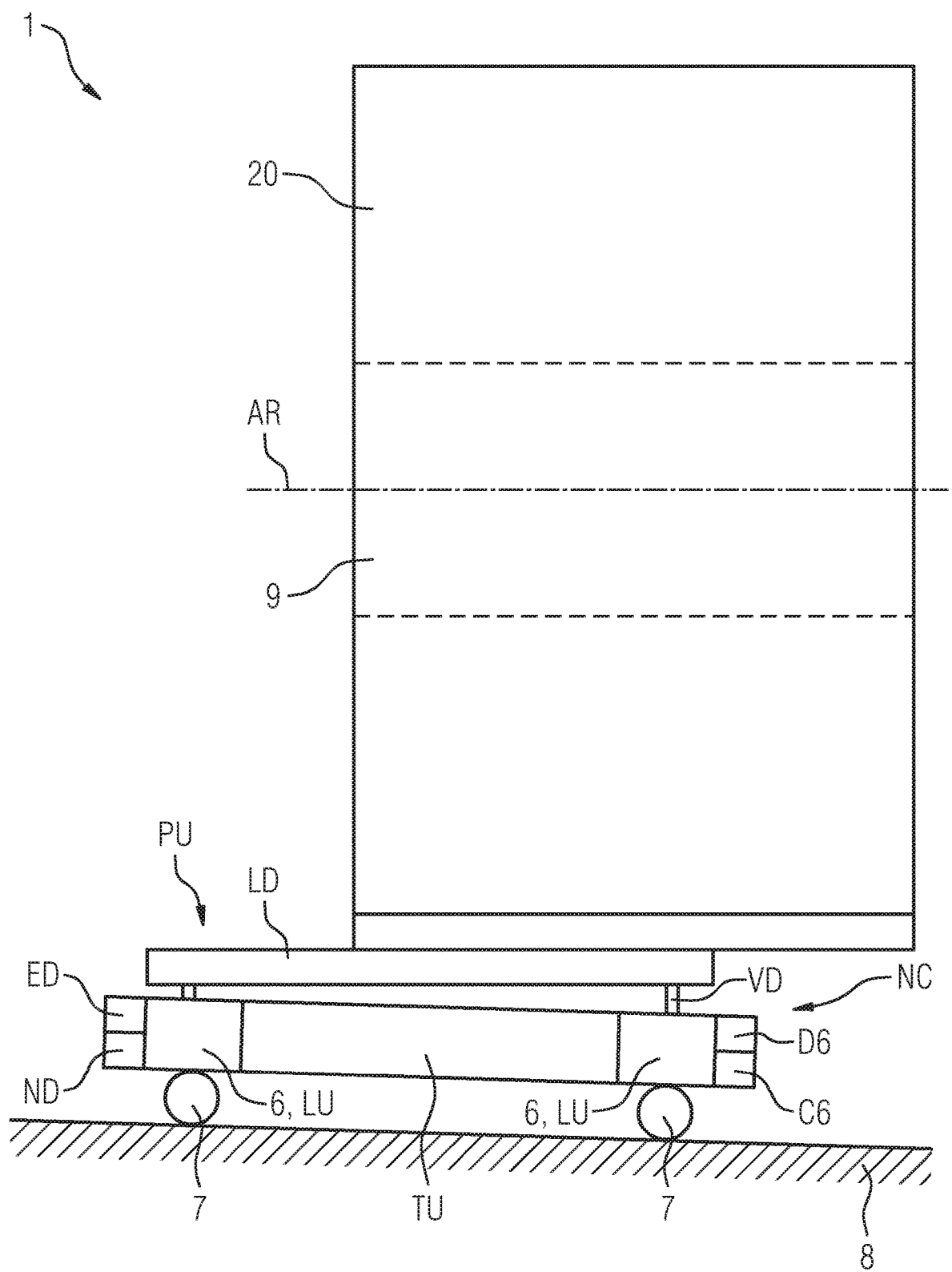
FIG. 5 shows a schematic representation of an arrangement according to a fourth embodiment variant of the invention.

FIG. 5 shows a schematic representation of an arrangement 1 according to a fourth embodiment variant of the invention. According to the fourth embodiment variant of the invention, the arrangement 1 includes a positioning unit PU arranged on the omnidirectional suspension 6 that is embodied to adjust a position of the gantry 20 relative to the omnidirectional suspension 6 and to adjust an orientation of the gantry 20 relative to the omnidirectional suspension 6. The positioning unit PU has a linear drive LD for the forward movement of the gantry 20 relative to the omnidirectional suspension 6. The positioning unit PU has a lifting device VD for the lifting movement of the gantry 20 relative to the omnidirectional suspension 6.

According to the fourth embodiment variant of the invention, the omnidirectional suspension 6 includes a loading unit TU that is embodied to load the gantry 20 and the positioning unit PU. According to the fourth embodiment variant of the invention, the arrangement 1 has a stabilizing unit for stabilizing a height of the gantry 20 and/or an inclination of the gantry 20 in order to correct any unevenness of the support 8. The stabilizing unit has an unevenness recording module ND for recording unevenness measurement data that relates to any unevenness of the support 8, and an unevenness correcting module NC for correcting unevenness on the basis of the unevenness measurement data. The unevenness correcting module NC is formed from the positioning unit PU and the first movement control module C6 of the movement control unit. The omnidirectional suspension 6 has an environment information recording module ED for recording environment information that relates to the environment of the omnidirectional suspension 6.

Figure 6:
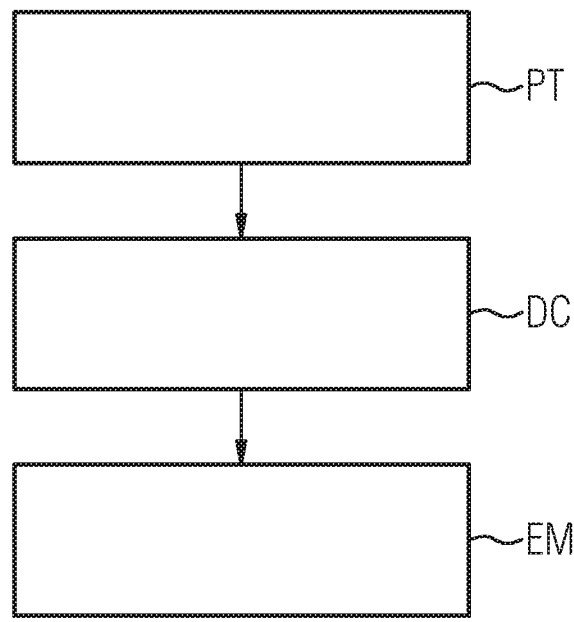
FIG. 6 shows a flowchart of method according to a fifth embodiment variant of the invention.

FIG. 6 shows a flowchart of a method according to a fifth embodiment variant of the invention.

The fifth embodiment variant of the invention relates to a method of executing a travel movement of an arrangement 1 that has a gantry 20 of a medical imaging device 2 and an omnidirectional suspension 6 for moving the arrangement 1 relative to a support 8, the method comprising:
  Provision PT of at least one target position,
  Determination DC of suspension control commands on the basis of the at least one target position, and
  Execution EM of the travel movement of the arrangement 1 via the omnidirectional suspension 6 on the basis of the suspension control commands.

Figure 7:
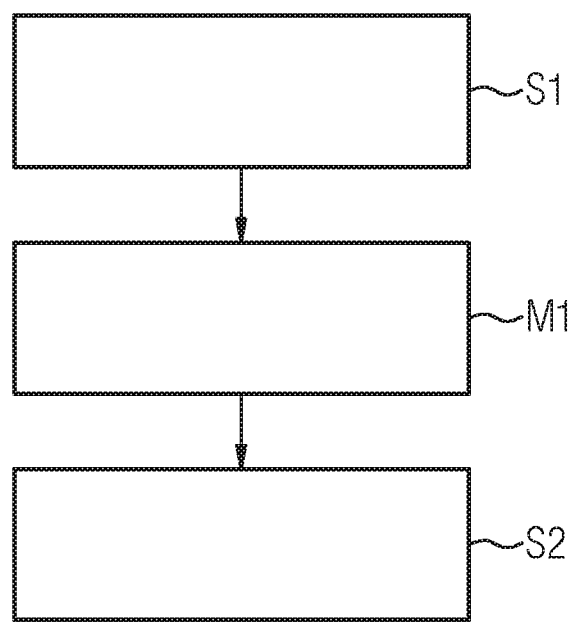
FIG. 7 shows a flowchart of a method according to a sixth embodiment variant of the invention.

FIG. 7 shows a flowchart of a method according to a sixth embodiment variant of the invention.

The sixth embodiment variant of the invention relates to a method of executing a scanning movement of an imaging data acquisition unit that is arranged on a gantry 20 of a medical imaging device 2 relative to a patient who is positioned on a patient positioning device 10, the method comprising:
  Execution S1 of a first part of the scanning movement by the gantry 20 being displaced relative to the omnidirectional suspension 6 via a positioning unit PU that is arranged on an omnidirectional suspension 6,
  Execution M1 of a travel movement of the omnidirectional suspension 6 relative to the patient positioning device 10, along the direction of the scanning movement, Execution S1 of a second part of the scanning movement by the gantry 20 being displaced relative to the omnidirectional suspension 6 via the positioning unit PU.

According to the sixth embodiment variant of the invention, the direction of the scanning movement is parallel to the system axis AR. The system axis AR is horizontal, with an isocenter of the medical imaging device 2 being located on the system axis AR.

Figure 8:
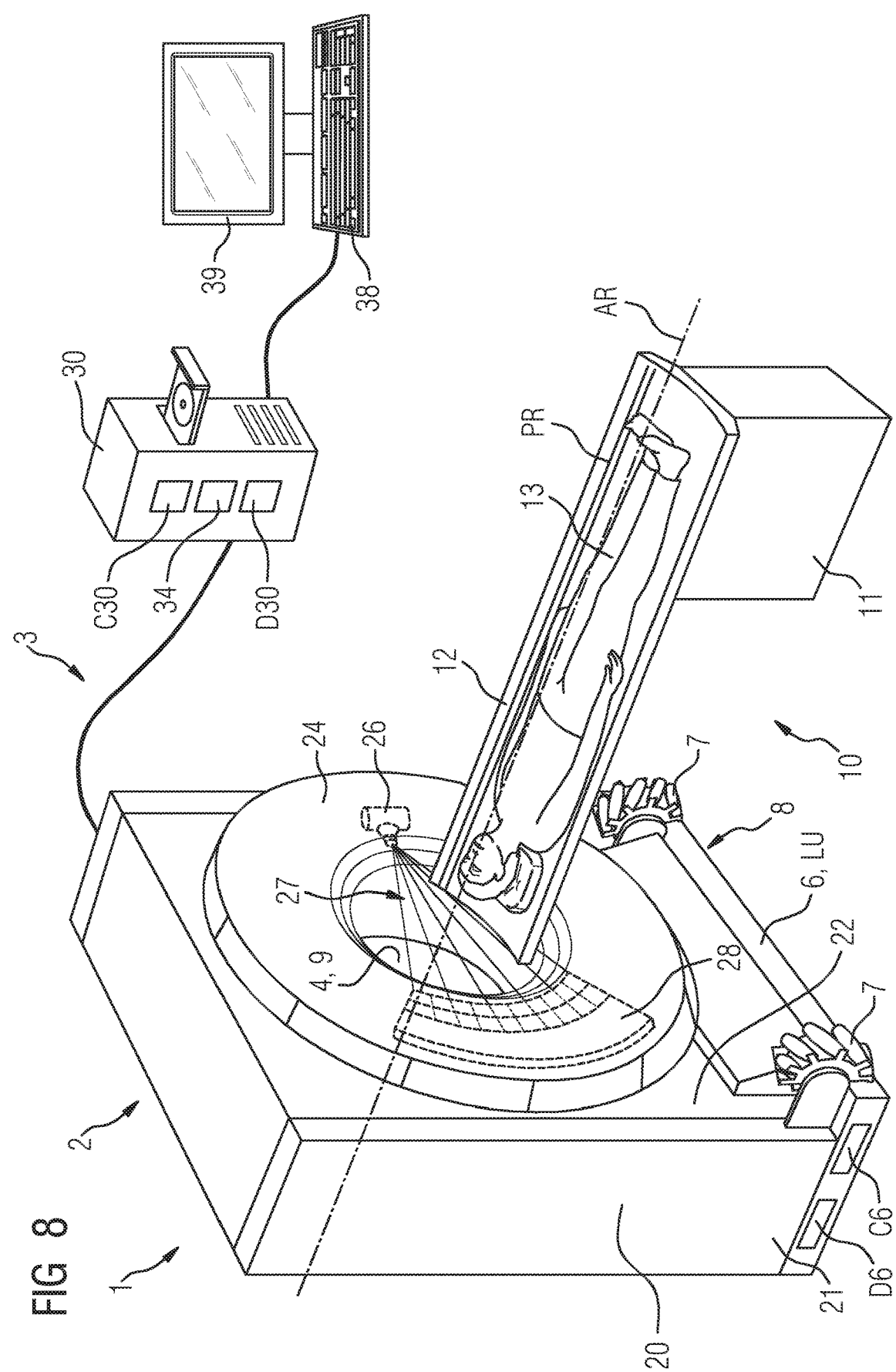
FIG. 8 shows a schematic representation of a system according to a seventh embodiment variant of the invention.

FIG. 8 shows a schematic representation of a system according to a seventh embodiment variant of the invention.

The seventh embodiment variant of the invention relates to a system comprising
- an arrangement 1 according to an embodiment variant of the invention,
- a movement control unit that is embodied to control the omnidirectional suspension 6 and/or the positioning unit PU,
- the patient positioning unit 10 and the medical imaging unit 2.

The system is embodied to execute a method according to an embodiment variant of the invention. The movement control unit has a first movement control module C6 that is integrated into the omnidirectional suspension 6 and a second movement control module C30 that is integrated into the control device 30.

The arrangement 1 has a data transfer unit D6 for the transfer of data from the omnidirectional suspension 6 and to the omnidirectional suspension 6 and for the transfer of data from the gantry 20 and to the gantry 20. In particular, it is possible for control data for the control of components of the arrangement 1, for example components of the omnidirectional suspension 6, of the positioning unit PU and components of the gantry 20, to be transferred between the arrangement 1 and the control device, and for imaging data captured via the imaging data acquisition device to be transferred between the arrangement 1 and the control device via the data transfer unit D6 and the data transfer module D30 of the control device 30.

The seventh embodiment variant of the invention provides that a position reference unit PR is arranged in the area of the patient positioning device 10 as a position reference for an image reconstruction in such a way that imaging data which relates to the position reference unit PR can be acquired during the execution of a method according to an embodiment variant of the invention.

Without limiting the general inventive concept, a computed tomography device is shown as an example of the medical imaging device 2. The medical imaging device 2 has the gantry 20, the tunnel shaped opening 9, the patient positioning device 10 and the control device 30. The gantry 20 has the fixed supporting frame 21 and the rotor 24. The rotor 24 is arranged so as to be rotatable about a rotating axis relative to the fixed supporting frame 21 via a rotatable positioning device. The patient 13 can be introduced into the tunnel shaped opening 9. The acquisition area 4 is located in the tunnel shaped opening 9. It is possible to position an area of the patient 13 in the acquisition area 4 in such a way that the radiation 27 from the radiation source 26 can reach the area to be displayed and can reach the radiation detector 28 after interacting with the area to be displayed. The patient positioning device 10 has the positioning table 11 and the transfer plate 12 for positioning the patient 13. The transfer plate 12 is movably arranged on the positioning table 11 in such a way relative to the positioning table 11 that the transfer plate 12 can be introduced into the acquisition area 4 in a longitudinal direction of the transfer plate 12, in particular along the system axis AR.

The medical imaging device 2 is embodied to acquire imaging data on the basis of electromagnetic radiation 27. The medical imaging device 2 has an imaging data acquisition unit. The imaging data acquisition unit is a projection data acquisition unit with the radiation source 26, e.g. an X-ray source, and the detector 28, e.g. an X-ray detector, in particular an energy resolved X-ray detector. The radiation source 26 is arranged on the rotor 24 and embodied to emit radiation 27, e.g. X-ray radiation, with radiation quanta 27. The detector 28 is arranged on the rotor 24 and is embodied to detect the radiation quanta 27. The radiation quanta 27 can reach from the radiation source 26 to the area to be displayed of the patient 13 and reach the detector 28 after interaction with the area to be displayed. In this way it is possible, via the imaging data acquisition unit, to acquire imaging data of the area to be displayed in the form of projection data.

The control device 30 is embodied to receive the imaging data acquired from the imaging data acquisition unit. The control device 30 is embodied to control the medical imaging device 2. The control device 30 has the image reconstruction device 34. A medical image dataset can be reconstructed on the basis of the imaging data via the image reconstruction device 34. The medical imaging device 2 has an input device 38 and an output device 39, each of which is connected to the control device 30. The input device 38 is embodied to feed control information, e.g. image reconstruction parameters, examination parameters, of the at least one target position for the omnidirectional suspension or similar. The output device 39 is in particular embodied to give out control information and images and/or to emit sounds.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An arrangement, comprising:
a gantry of a medical imaging device;
an omnidirectional suspension configured to move the arrangement relative to a support;
a positioner arranged on the omnidirectional suspension and having a linear drive for forward movement of the gantry relative to the omnidirectional suspension; and
a memory storing computer instructions and one or more processors configured to execute computer readable instructions, the one or more processors being configured to perform operations including:
executing a first part of a scanning movement by displacing the gantry, disposed around a patient couch, relative to the omnidirectional suspension via the positioner;
executing a travel movement of the omnidirectional suspension relative to the patient couch along a direction of the scanning movement; and
executing a second part of the scanning movement by displacing the gantry, disposed around a patient couch, relative to the omnidirectional suspension via the positioner, wherein
the medical imaging device is selected from a group of imaging modalities consisting of an X-ray device, a C-arm X-ray device, a computed tomography device, a single photon emission computed tomography device, a positron emission tomography device, and combinations thereof,
the scanning movement can be executed along a system axis of the medical imaging device or along a longitudinal direction of the patient couch; and
the first part and the second part of the scanning movement are executed in each case by the gantry being displaced relative to the omnidirectional suspension via the linear drive.

2. The arrangement of claim 1, wherein the omnidirectional suspension includes at least one of:
at least one omnidirectional wheel, and
at least one omnidirectional omnidrive module.

3. The arrangement of claim 1, wherein the omnidirectional suspension includes at least one of
a set of omniwheels, and
a set of Mecanum wheels.

4. The arrangement of claim 1,
the positioner is configured to adjust at least one of
a position of the gantry relative to the omnidirectional suspension and
an orientation of the gantry relative to the omnidirectional suspension.

5. The arrangement of claim 4, wherein the positioner includes a lift for a lifting movement of the gantry relative to the omnidirectional suspension.

6. The arrangement of claim 4, wherein the omnidirectional suspension includes a load receiver embodied to receive at least one of the gantry and the positioner.

7. The arrangement of claim 4, wherein the omnidirectional suspension includes a loader embodied to load at least one of the gantry and the positioner.

8. The arrangement of claim 1, further comprising:
a stabilizer configured to stabilize at least one of a height and an inclination of the gantry in order to correct any unevenness of the support.

9. The arrangement of claim 8, wherein the stabilizer includes a memory storing computer instructions and one or more processors to execute computer readable instructions, the one or more processors being configured to perform operations including recording unevenness measurement data that relates to unevenness of the support and correcting unevenness based upon the unevenness measurement data.

10. The arrangement of claim 1, wherein the omnidirectional suspension includes a memory storing computer instructions and one or more processors to execute computer readable instructions, the one or more processors being configured to perform operations including recording environment information that relates to an environment of the omnidirectional suspension.

11. The arrangement of claim 1, wherein the omnidirectional suspension is embodied for at least one of autonomous travel and semiautonomous travel.

12. The arrangement of claim 1, further comprising:
an energy storage unit to supply power to at least one of the omnidirectional suspension and the gantry.

13. The arrangement of claim 1, further comprising:
a data transfer unit configured to transfer data from at least one of the omnidirectional suspension and the gantry and to transfer data to at least one of the omnidirectional suspension and the gantry.

14. The arrangement of claim 1, further comprising:
an air flow guidance unit to guide an air flow for cooling a component of the gantry, wherein the air flow guidance unit includes at least one exit for the air flow in an area of the support.

15. The arrangement of claim 1, further comprising:
a cooling fluid attachment unit, embodied to at least one of receive and release a cooling fluid for cooling a component of the gantry.

16. A method of executing a travel movement of arrangement of claim 1, the arrangement including a gantry of a medical imaging device and an omnidirectional suspension configured to move the arrangement relative to a support, the method comprising:
provisioning at least one target position;
determining suspension control commands based upon the at least one target position; and
executing the travel movement of the arrangement, via the omnidirectional suspension, based upon the suspension control commands.

17. The method of claim 16, further comprising:
recording at least one item of environment information relating to an environment of the omnidirectional suspension, wherein the determining of the suspension control commands includes determining the suspension control commands based upon the at least one target position and the at least one item of environment information.

18. The method of claim 16, wherein the determining of the suspension control commands involves adaptive route planning.

19. The method of claim 17, wherein at least one of
the recording includes recording at least one item of environment information autonomously by the omnidirectional suspension; and
the determining of the suspension control commands includes determining the suspension control commands autonomously by the omnidirectional suspension.

20. The arrangement of claim 2, wherein the omnidirectional suspension includes at least one of
a set of omniwheels, and
a set of Mecanum wheels.

21. The arrangement of claim 1, wherein the omnidirectional suspension includes a load receiver embodied to receive the gantry.

22. The arrangement of claim 1, wherein the omnidirectional suspension includes a loader embodied to load the gantry.

23. The arrangement of claim 4, further comprising:
a stabilizer configured to stabilize at least one of a height and an inclination of the gantry in order to correct any unevenness of the support.

24. The arrangement of claim 23, wherein the stabilizer includes a memory storing computer instructions and one or more processors to execute computer readable instructions, the one or more processors being configured to perform operations including recording unevenness measurement data that relates to unevenness of the support and correcting unevenness based upon the unevenness measurement data.

25. The arrangement of claim 1, further comprising:
an air flow guidance unit to guide an air flow for cooling the component of the gantry, wherein the air flow guidance unit includes at least one exit for the air flow in an area of the support.

26. The arrangement of claim 25, further comprising:
a cooling fluid attachment unit, embodied to at least one of receive and release a cooling fluid for cooling the component of the gantry.

27. The arrangement of claim 1, further comprising:
a cooling fluid attachment unit, embodied to at least one of receive and release a cooling fluid for cooling the component of the gantry.

28. The method of claim 17, wherein the determining of the suspension control commands involves adaptive route planning.

29. The method of claim 16, wherein the suspension control commands are determined autonomously by the omnidirectional suspension.

30. A method of executing a scanning movement of a radiation source and a radiation detector arranged on a gantry of a medical imaging device relative to a patient positioned on a patient couch, the gantry being adjustably mounted relative to a support via an omnidirectional suspension, the medical imaging device is selected from a group of imaging modalities consisting of an X-ray device, a C-arm X-ray device, a computed tomography device, a single photon emission computed tomography device, a positron emission tomography device, and combinations thereof, the method comprising:
executing the scanning movement by the omnidirectional suspension moving the gantry, disposed around the patient couch, relative to the patient couch, wherein the scanning movement is executed in a first part of by displacing the gantry relative to the omnidirectional suspension via a positioner arranged on the omnidirectional suspension;
a travel movement of the omnidirectional suspension relative to the patient couch is executed along a direction of the scanning movement; and
the scanning movement is executed in a second part by displacing the gantry, disposed around the patient couch, relative to the omnidirectional suspension via the positioner, and wherein
the scanning movement is executed along a system axis of the medical imaging device or along a longitudinal direction of the patient couch, and
the positioner has a linear drive for forward movement of the gantry relative to the omnidirectional suspension and that the first part and the second part of the scanning movement are executed in each case by the gantry being displaced relative to the omnidirectional suspension via the linear drive.

31. A method of executing a scanning movement of a radiation source and a radiation detector arranged on a gantry of a medical imaging device relative to a patient positioned on a patient couch, the medical imaging device being selected from a group of imaging modalities consisting of an X-ray device, a C-arm X-ray device, a computed tomography device, a single photon emission computed tomography device, a positron emission tomography device, and combinations thereof, the method comprising:
executing a first part of the scanning movement by displacing the gantry, disposed around the patient couch, relative to an omnidirectional suspension via a positioner arranged on the omnidirectional suspension;
executing a travel movement of the omnidirectional suspension relative to the patient couch along a direction of the scanning movement; and
executing a second part of the scanning movement by displacing the gantry, disposed around the patient couch, relative to the omnidirectional suspension via the positioner, wherein
the scanning movement can be executed along a system axis of the medical imaging device or along a longitudinal direction of the patient couch, and
the positioner has a linear drive for forward movement of the gantry relative to the omnidirectional suspension and that the first part and the second part of the scanning movement are executed in each case by the gantry being displaced relative to the omnidirectional suspension via the linear drive.

* * * * *